(12) United States Patent
Frigg et al.

(10) Patent No.: US 6,231,576 B1
(45) Date of Patent: May 15, 2001

(54) FLAT INTRAMEDULLARY NAIL

(75) Inventors: Robert Frigg; Silvana Filoso; Peter Däscher, all of Davos Platz (CH)

(73) Assignee: Synthes (U.S.A.), Paoli, PA (US)

( * ) Notice: Subject to any disclaimer, the term of this patent is extended or adjusted under 35 U.S.C. 154(b) by 0 days.

(21) Appl. No.: 09/319,214

(22) PCT Filed: Dec. 2, 1996

(86) PCT No.: PCT/EP96/05324

§ 371 Date: Aug. 6, 1999

§ 102(e) Date: Aug. 6, 1999

(87) PCT Pub. No.: WO98/24380

PCT Pub. Date: Jun. 11, 1998

(51) Int. Cl.$^7$ .............................. A61B 17/68; A61B 17/72
(52) U.S. Cl. .................................. 606/62; 606/60; 606/64
(58) Field of Search .................................. 606/60, 62, 64, 606/65, 67

(56) References Cited

U.S. PATENT DOCUMENTS

| | | | |
|---|---|---|---|
| 2,834,342 | 5/1958 | Yost | 128/92 |
| 3,002,514 | 10/1961 | Deyerle | 128/92 |

(List continued on next page.)

FOREIGN PATENT DOCUMENTS

| | | |
|---|---|---|
| 587 317 | 10/1933 | (DE) . |
| 38 35 682 A1 | 4/1990 | (DE) . |
| 0 086 552 A1 | 8/1983 | (EP) . |
| 0 094 039 A1 | 11/1983 | (EP) . |
| 1071298 | 2/1984 | (SU) . |
| 1337074 A1 | 9/1987 | (SU) . |
| WO 98/05263 | 2/1998 | (WO) . |

OTHER PUBLICATIONS

W. L. Pugh, "A Self–Adjusting Nail–Plate for Fractures About the Hip Joint," J. Bone Joint Surg. 37–A:1085–93, (1955).

Richards et al., "The AO Dynamic HIP Screw and the Pugh Sliding Nail in Femoral Head Fixation," J. Bone Joint Surg. [Br] 72–B:794–6, (1990).

Jarrett et al., "The stable internal fixation of peritochanteric hip fractures," Part V (pp. 203–218).

Calandruccio et al., "Internal Fixation Devices for Fractures of the Proximal Femur American Academy of Orthopaedic Surgeons Committee on the History of Orthopaedic Surgery," Brochure (pp. 1–7).

William K. Massie, M.D., "Extracapsular Fractures of the Hip Treated by Impaction Using a Sliding Nail–plate Fixation," Chapter 18 (pp. 180–201).

*Primary Examiner*—Gene Mancene
*Assistant Examiner*—Michael B. Priddy
(74) *Attorney, Agent, or Firm*—Pennie & Edmonds LLP

(57) ABSTRACT

The intramedullary nail for treating a fracture of a long bone according to the present invention has the shape of a helically twisted blade with a flattened cross section extending partially or totally along the longitudinal axis of the nail. The nail is provided with a hole at its distal end for receiving a bone fixation means to be inserted transversely through the hole and at least one cortex of the long bone. The nail is made long and thin with the smallest dimension of the cross section being much smaller than the largest dimension, so that it is flexible along the longitudinal axis of the nail.

20 Claims, 3 Drawing Sheets

U.S. PATENT DOCUMENTS

| | | | | |
|---|---|---|---|---|
| 3,025,853 | * | 3/1962 | Mason | 606/67 |
| 3,029,811 | | 4/1962 | Yost | 128/92 |
| 3,561,437 | | 2/1971 | Orlich | 128/92 |
| 4,055,172 | * | 10/1977 | Ender et al. | 606/62 |
| 4,483,335 | * | 11/1984 | Tornier | 606/64 |
| 4,628,923 | | 12/1986 | Medoff | 128/92 |
| 4,667,663 | * | 5/1987 | Miyata | 606/62 |
| 4,776,330 | | 10/1988 | Chapman et al. | 128/92 |
| 4,794,919 | * | 1/1989 | Nilsson | 606/65 |
| 4,908,032 | | 3/1990 | Keller | 623/16 |
| 4,915,092 | * | 4/1990 | Firica et al. | 606/67 |
| 4,978,349 | | 12/1990 | Frigg | 606/67 |
| 5,002,544 | | 3/1991 | Klaue et al. | 606/69 |
| 5,032,125 | | 7/1991 | Durham et al. | 606/62 |
| 5,034,012 | | 7/1991 | Frigg | 606/62 |
| 5,047,029 | | 9/1991 | Aebi et al. | 606/61 |
| 5,116,335 | * | 5/1992 | Hannon et al. | 606/62 |
| 5,116,336 | | 5/1992 | Frigg | 606/65 |
| 5,133,718 | * | 7/1992 | Mao | 606/69 |
| 5,295,991 | | 3/1994 | Frigg | 066/62 |
| 5,300,074 | | 4/1994 | Frigg | 128/67 |
| 5,312,402 | | 5/1994 | Schläpfer et al. | 606/53 |
| 5,437,666 | | 8/1995 | Tepic et al. | 606/55 |
| 5,443,466 | * | 8/1995 | Shah | 606/62 |
| 5,462,547 | | 10/1995 | Weigum | 606/65 |
| 5,498,264 | | 3/1996 | Schlapfer et al. | 606/72 |
| 5,501,684 | | 3/1996 | Schlapfer et al. | 606/73 |
| 5,534,001 | | 7/1996 | Schlapfer et al. | 606/61 |
| 5,591,168 | | 1/1997 | Judet et al. | 606/65 |
| 5,618,286 | * | 4/1997 | Brinker | 606/60 |
| 5,741,256 | * | 4/1998 | Bresina | 606/62 |

* cited by examiner

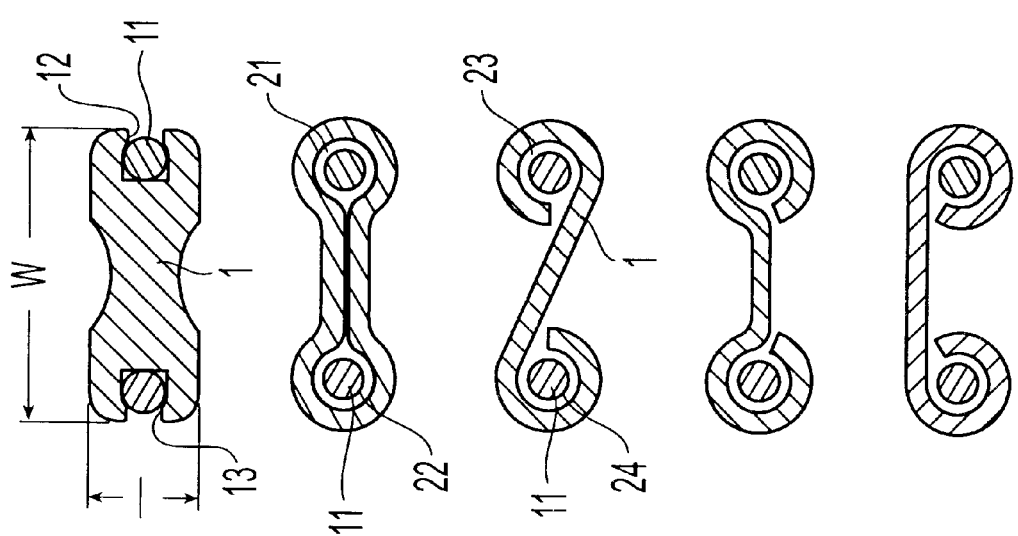
Fig. 8
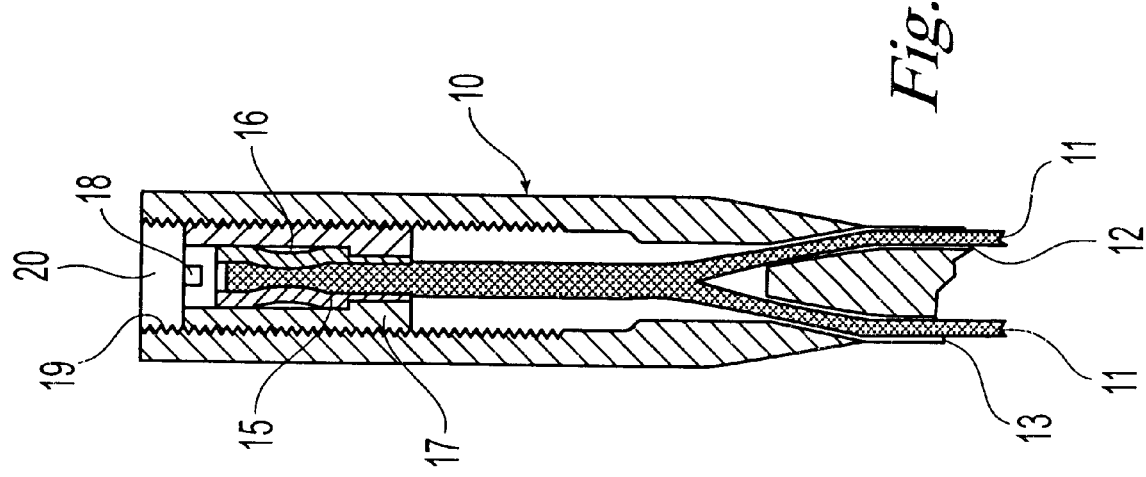
Fig. 3
Fig. 4
Fig. 5
Fig. 6
Fig. 7

FLAT INTRAMEDULLARY NAIL

FIELD OF THE INVENTION

This invention relates to an intramedullary nail having the shape of a helically twisted blade and at least one hole at one of its free ends. The intramedullary nail is especially suited for the humerus and for other long bones where the insertion plane is different from the locking plane. It is also suited for long bones of young children where the growth plate should not be disturbed.

BACKGROUND OF THE INVENTION

In recent years, the intramedullary nail has gradually gained importance and is becoming a standard method of internal fixation. Since the development of this method by K üntscher, the intramedullary nail has broadened its range of indications (e.g. locking nail, Gamma nail, reconstruction nail).

The basic concept behind nailing has remained the same, namely the introduction of a tube or full cylinder into the medullary cavity of a tubular bone. Initially, nailing was used for the femur, but now, its application has been extended to include all large tubular bones. Until now, the cross-sections of intramedullary nails have remained more or less the same. Even the cloverleaf cross-section developed by Küntscher some 50 years ago is still being used today, even though it has been proven that this shape brings no special advantages. Additionally, changing the cross-section from the circular or almost circular cross-section was never considered necessary before, since the medullary cavity of the various tubular bones was usually opened using a rotating or circular cutting device.

Today, more attention is being paid to the rate of fracture healing, and it is believed that healing occurs faster if less damage is done to the bone during placement of an implant in the body. By choosing an appropriate cross-sectional shape for an intramedullary nail which corresponds to the anatomy of the medullary canal, it is possible to eliminate unnecessary removal of bone and tissue from the medullary canal, thus promoting healing by minimizing damage to the medullary canal and its vascularization.

The choice of nail cross-section is particularly relevant for the humerus bone, in which the medullary canal is not round along its entire length but is in fact flat and thin in the distal part. For this bone, a nail with the typical circular or almost circular cross-section would not be appropriate. A nail with a flattened cross-section would be more suited for the distal humerus.

SUMMARY OF THE INVENTION

The opening of the medullary canal for insertion of the nail can also cause unnecessary damage to the bone, as well as to the surrounding soft tissue and joint. Intramedullary nails are typically stiff and are traditionally inserted through an insertion site which is in line with the longitudinal axis of the bone.

For the case of the humerus bone, antegrade insertion (i.e. insertion from the shoulder end of the humerus) typically goes directly through the rotator cuff. This can cause irreparable damage to the joint capsule and instability of the shoulder joint, and can result in post-operative pain and/or loss of range of motion of the limb.

For the case of growing young bones, insertion sites in line with the longitudinal axis of the bone tend to interfere with the growth plate, which can affect the normal development and growth of the bone. An "ideal" insertion site avoids both the joint for long bones, as well as the growth plate in young patients. For the humerus, an ideal antegrade insertion site is located slightly distal to the greater trochanter on the lateral aspect, thus completely avoiding the joint capsule and rotator cuff at the shoulder. This ideal insertion site can not be used with traditionally stiff nails, and could only be used with nails which would be flexible along their length.

The invention as claimed aims at solving the above described problems by providing an intramedullary nail whose flexibility is achieved by relying on the natural mechanical properties (i.e, modulus of elasticity) of the nail material.

The nail is made long and thin with the smallest dimension of the cross-section being much smaller than the largest dimension, so that it is flexible along the longitudinal axis of the nail.

If such a thin, flat nail is inserted into the humerus using the ideal, antegrade, lateral insertion site described above, the distal part of the flat nail will be oriented 90° to the flat distal humerus. In order to correct this orientation problem of the flat distal nail in the flat distal humerus, the nail is twisted 90°, or any multiple of 90°, along its length. This does not significantly affect the local bending properties of the nail (i.e. short length along the axis), since bending can still occur at any one longitudinal section. Retrograde insertion (i.e. insertion from the elbow end of the humerus) of this flat nail into the humerus is not affected by this twist, since the proximal humerus is relatively large, has a round cross-section, and allows the distal part of the nail to be oriented in any way inside the proximal humerus. Therefore, this flat, twisted nail is suitable for both antegrade and retrograde insertion into the humerus.

For long, thin, flat nails, the 90° twist of the nail has an additional advantage: to bring added bending stability to the longitudinal device. A flat longitudinal device, after implantation, may bend in the medullary canal under a bending load. With an added longitudinal twist, however, the device is more stable longitudinally and is, thus, less likely to bend in the canal during normal limb activity.

For thin, flat nails, the 90° twist of the nail has yet another advantage, related to locking for both an antegradely- or retrogradely-inserted nail. For a locking hole to be designed through a nail, the cross-sectional dimension orthogonal to the hole axis must be greater than the diameter of the locking hole. Depending of course on the diameter of the locking bolt, this may not be possible for the thin, flat nail design if the locking hole goes through the largest dimension of the cross-section, i.e. through the thickest wall. From an anatomical point of view, the presence of nerves and other important tissues can also limit the possibility of locking directions. In the proximal humerus, the brachial plexus nerve group located antero-medially should be avoided during locking. Thus, for a retrograde nail, the safest locking in the proximal humerus is in the lateral-medial direction. In contrast, for an antegrade nail, locking in the flat distal humerus is most commonly done in the posterior-anterior direction, i.e. through the thinnest wall of the humerus.

Therefore, to satisfy anatomical and mechanical requirements for locking, the proximal and distal locking holes and screws should be oriented 90° (or a multiple of 90°) to each other.

For a thin, flat cross-section such as for the invention described here, this can only be achieved with a nail which is twisted 90°, or multiple of 90°, along its length.

For the purpose of closing a fracture gap, a wire or cable loop, as described in U.S. Pat. No. 5,034,012, can be added to the nail according to the invention.

The wire/cable can be looped around the entire length of the nail, preferably inset in slots, grooves or other shape of opening on the narrow sides of the flat cross-section of the nail. The closed end of the wire or cable (i.e. the looped part) at the distal tip of the nail is protected from being damaged or deformed during insertion by a metal U-shaped part surrounding it, which is part of the nail. The two ends of the wire/cable at the open end of the loop are fixed inside a nut, which is inside the proximal part of the nail. To reduce a fracture gap using this wire/cable loop design in the flat, thin nail design, the locking bolt is first placed at the far end of the nail through the locking hole and the loose wire/cable loop. The inner nut is then rotated counter-clockwise with a screwdriver, causing the nut to move upwards and the wire/cable to be pulled upwards. As this is done, the wire/cable loop around the locking bolt at the distal part of the nail becomes smaller, tightly encloses the locking bolt, and finally pulls the locking bolt towards the proximal part of the nail. This applies a compressive force between the proximal and distal bone fragments, thus reducing the fracture gap.

To summarize the important points, the first main advantage of the flattened, twisted nail is that it is flexible in bending, which allows it be inserted from more anatomical insertion sites not necessarily in line with the longitudinal axis of the bone. As explained above, this is particularly important for the proximal humerus to avoid the shoulder joint capsule and rotator cuff, as well as for pediatric long bones where the growth plate should be avoided. The twist allows not only locking advantages but also makes the nail generally more stable in bending after insertion into the medullary canal.

Another main advantage of this nail is that its flat, thin cross-section, when used in the humerus, corresponds to the shape of the medullary cavity of the distal humerus. It therefore requires no extra bone or tissue to be removed before nail insertion. As well, the small, anatomical cross-section does not significantly disturb the vascularization in the medullary canal, which is important for fracture healing.

The various features of novelty which characterize the invention are pointed out with particularity in the claims annexed to and forming part of this disclosure. For the better understanding of the invention, its operating advantages and specific objects attained by its use, reference should be had to the accompanying drawings, examples and descriptive matter in which are illustrated and described preferred embodiments of the invention.

BRIEF DESCRIPTION OF THE DRAWINGS

In the drawing:

FIG. 3 is a cross-section of the nail according to FIG. 1 at the line III—III;

FIG. 4 is a modified cross-section of the nail according to the invention;

FIG. 5 is a further modified cross-section of the nail according to the invention;

FIG. 6 is a further modified cross-section of the nail according to the invention;

FIG. 7 is a further modified cross-section of the nail according to the invention;

FIG. 8 is a partial longitudinal cross-section through the upper part of the nail according to FIG. 1.

DETAILED DESCRIPTION OF THE PREFERRED EMBODIMENTS

Figures 1, 2:
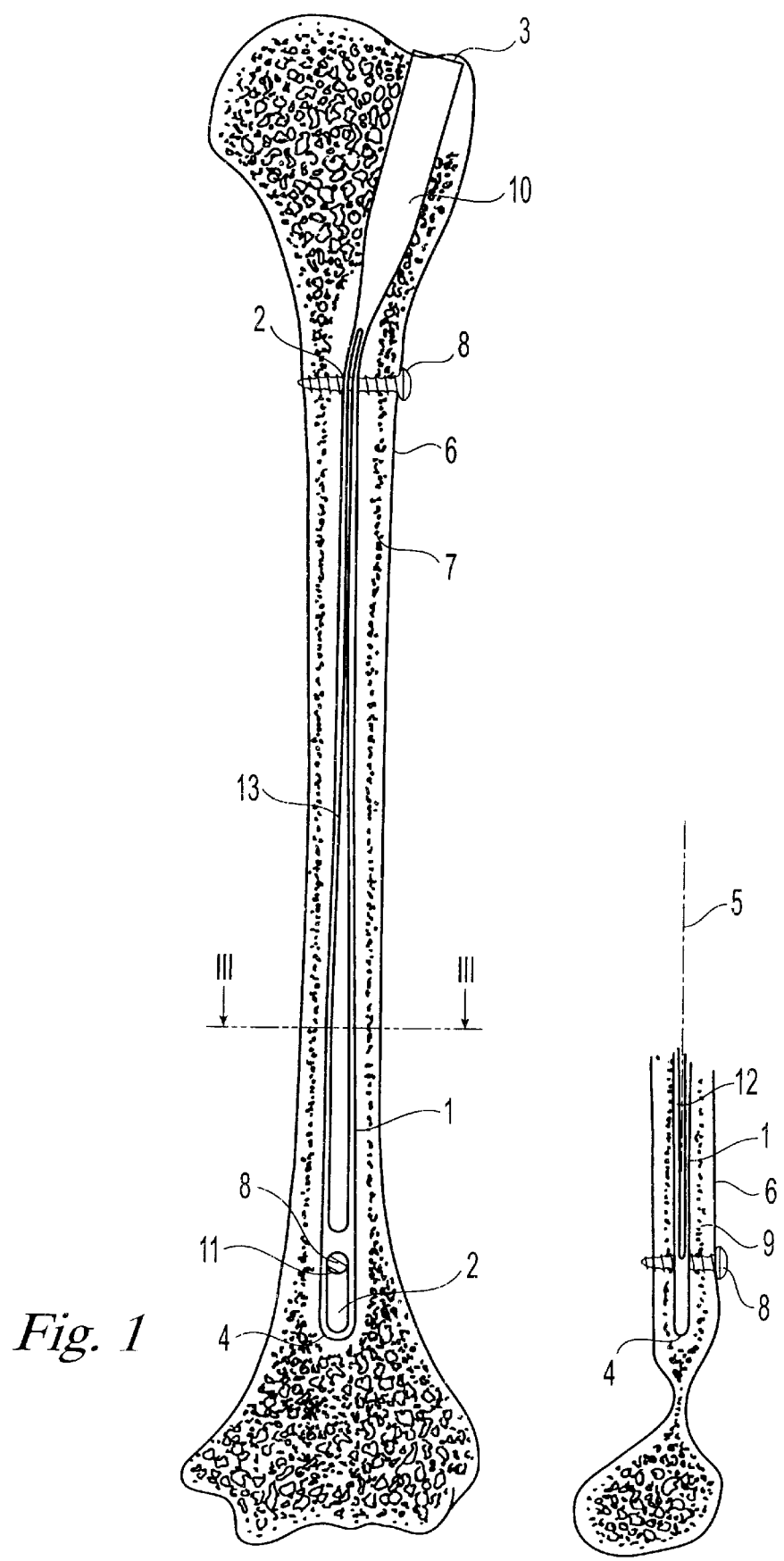
FIG. 1 is a perspective view of the intramedullary nail according to the invention, shown inserted antegradely into humerus and locked distally with a locking screw.
FIG. 2 is a partial representation of the lower part of the nail according to FIG. 1 seen from an 90° angle.

FIGS. 1 to 3 show an intramedullary nail consisting of a helically twisted blade 1 having a hole 2 at its distal end 4. The nail may have a further hole 2 towards its proximal end 3. The blade 1 is twisted about 90° around its longitudinal axis 5 in a continuous way.

The length L of the blade 1 is in the range of 150 to 300 mm and the ratio T/W between the thickness T and width W of said blade 1—as represented in FIG. 3—is in the range of 0,035 to 0,286, preferably in the range of 0,1 to 0,2.

The flat intramedullary nail is used conventionally as shown in FIGS. 1 and 2 for treating a fracture of a long bone 6 by inserting it longitudinally into the medulla 7 of a long bone 6, and securing the intramedullary nail to the long bone 6 in its longitudinal position by bone fixation means 8, preferably in the form of screws, to be inserted transversally through the hole 2 and at least one cortex 9 of the long bone 6.

The head 10 at the proximal end 3 of the intramedullary nail is shown in more detail in FIG. 8 in order to describe how to assemble the intramedullary nail of FIG. 1. One end of a preferably metallic cable (or wire) 11 is inserted through the head 10 and then threaded through groove 12 on the right side of the nail until it exits into hole 2 as shown in more detail in FIG. 9. The one end of cable 11 pushed into hole 2 is then threaded back up through groove 13 on the left side of the nail until it exits in the head 10.

At this point both ends of cable 11 are protruding out of head 10 at the proximal end of the nail, and towards the distal end 4 of the nail, cable 11 forms a loop at locking hole 2.

Figure 9:
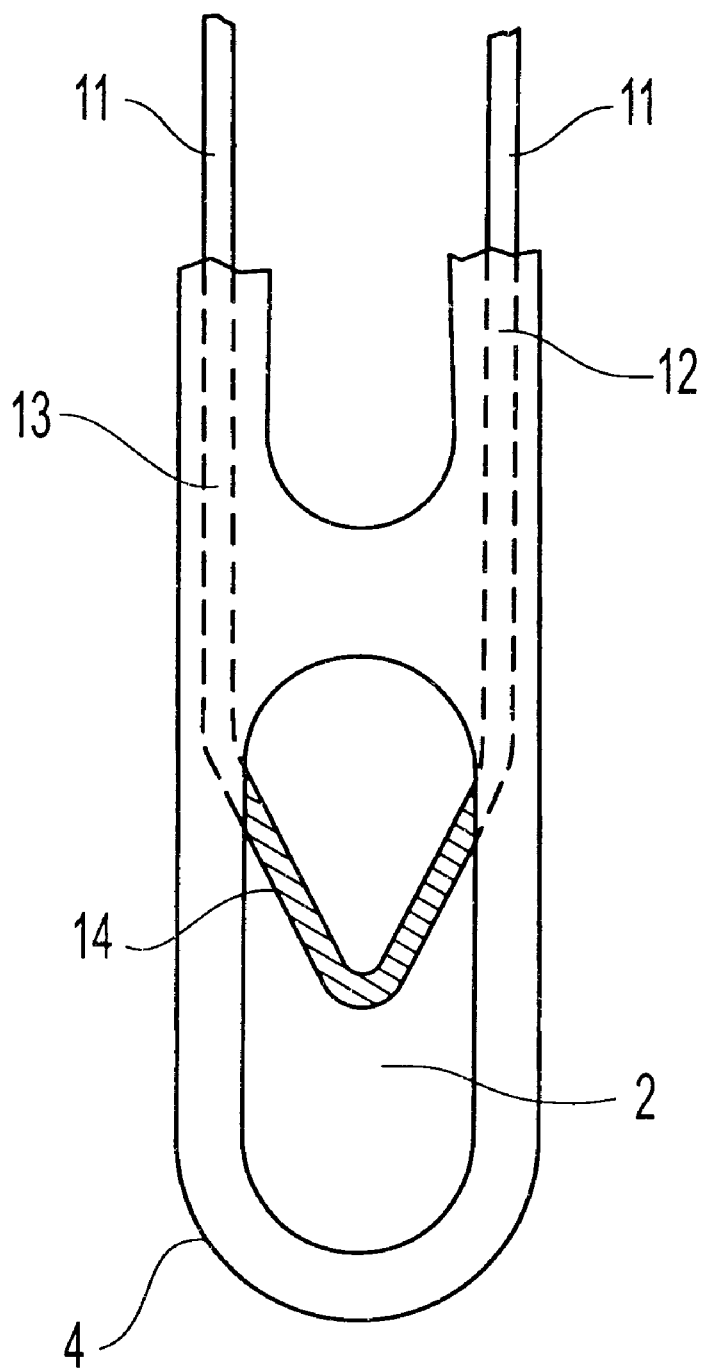
FIG. 9 is partial enlarged representation of the lower part of the nail according to FIG. 1 with the cable in the lowest position.

Both ends of cable 11 are then inserted into the cavity of an inner hollow tube 15. To secure cable 11 in said inner tube 15 the cable 11 is first adjusted for length and then inner tube 15 is deformed at position 16 in at least one plane. Threaded tube 17 is slid over inner tube 15 and the assembly 15,17 is threaded into the interior threads 19 of hollow head 10 by means of tool geometry 18, resulting in twisting of cable 11, until threaded tube 17 is at its lowest position inside head 10. If the cable length was properly adjusted before being fixed inside inner tube 15, the loop 14 of cable 11 will now be at its lowest position inside slot 2 at the distal end 4 of the nail as shown in FIG. 9. The nail is now assembled and ready for implantation in the intramedullary cavity of a long bone.

An insertion handle (not shown) is fixed on head 10 of the nail using the interior threads 19. The nail is implanted in the usual fashion in the humerus or other long bone in the body. The insertion handle is removed. The nail is now ready to be locked distally.

Free-hand distal locking is performed through slot 2 in the usual fashion with a locking bolt or screw 8. The elongated hole or slot 2 is easier to locate for, compared to traditional holes, resulting in easier free-hand locking. After distal locking, a tool (not shown), e.g. a slotted screwdriver is used at tool geometry 18 through open end 20 of head 10 to unthread (or raise) threaded tube 17 until the loop 14 of cable 11 in slot 2 contacts and applies pressure to the locking bolt or screw 8 as shown in FIG. 1.

The advantage of the nail according FIG. 1 over nails according to the prior art, e.g. 7 mm diameter nails, is the easier free-hand distal-locking due to the elongated hole 2, while still offering the advantage of secure bolt/screw fixation, provided by the loop 14 of cable 11 around the bolt/screw.

The configuration of blade 1 of the nail can be varied in several ways.

FIG. 3 shows the embodiment with lateral grooves 12 and 13 guiding cable 11.

FIG. 4 shows an alternative embodiment in which the grooves 12 and 13 of FIG. 3 are replace by closed tunnels in which cable 11 is lodged.

FIG. 5 shows a further embodiment which is interesting from a point of view of manufacturing. It consist of a simple metal sheet forming blade 1 the lateral side of which have been curved in order to form lateral tunnels taking up cable 11.

FIGS. 6 and 7 are just other variations of the embodiment according to FIG. 5 and which are easy to manufacture.

The advantage of the nail according FIG. 1 over prior art small-diameter flexible nails, e.g. 2 to 4 mm, is that it offers improved stability due to the interlocking possibilities. Interlocking is usually not possible for small-diameter nails, due to the material limitation. In other words, there is not enough material to insert a locking screw through it.

While the foregoing description and drawings represent the preferred embodiments of the present invention, it will be obvious for those skilled in the art that various changes and modifications may be made therein without departing from the true spirit and scope of the present invention.

What is claimed is:

1. An intramedullary nail having a longitudinal axis for fixation of a fractured bone having a medullary canal, the intramedullary nail comprising a helically twisted blade of predetermined thickness, length and width and having a distal end with a distal hole for receiving a first bone fixation element for securing the distal end to the bone and a proximal end with a proximal hole for receiving a second bone fixation element for securing the proximal end to the bone, wherein at least a portion of the blade has a flatten cross section extending along the longitudinal axis of the nail and through the medullary canal of the bone and wherein the proximal and distal ends lie substantially within the medullary canal.

2. The intramedullary nail of claim 1 wherein the ratio of blade thickness to blade width is about 0.035 to 0.286.

3. The intramedullary nail of claim 1 wherein the blade twists from about 30° to 200° about a longitudinal axis of the blade.

4. The intramedullary nail of claim 3 wherein the blade twists continuously about the longitudinal axis of the blade.

5. The intramedullary nail of claim 1 further comprising an insertion element located at the proximal end of the blade for inserting and removing the intramedullary nail from the bone.

6. The intramedullary nail of claim 5 wherein the insertion element comprises an internally threaded portion on the proximal end of the blade for receiving a threaded insertion handle.

7. The intramedullary nail of claim 1 wherein the first and second bone fixation elements each comprise a cortical screw.

8. The tramedullary nail of claim 1 wherein the proximal and distal holes are perpendicular with respect to the longitudinal axis of the intramedullary nail.

9. The intramedullary nail of claim 1 wherein the distal hole is elongated along a longitudinal axis of the nail.

10. The intramedullary nail of claim 1 wherein the blade length is from about 150 to 300 mm.

11. The intramedullary nail of claim 1 wherein the blade cross section is elliptical.

12. The intramedullary nail of claim 1 wherein a largest dimension of the blade cross section is from about 6 to 20 mm.

13. The intramedullary nail of claim 1 wherein the blade width is no less than about 0.3 to 5 mm.

14. The intramedullary nail of claim 1 wherein the intramedullary nail is made of sheet metal or tubing having a wall thickness from about 0.2 to 3.5 mm.

15. The intramedullary nail of claim 1 wherein the intramedullary nail is made of a polymeric sheet having a wall thickness from about 0.5 to 5 mm.

16. The intramedullary nail of claim 1 further comprising a pair of channels in the blade for receiving a cable or wire for closing a fracture gap in the fractured bone.

17. The intramedullary nail of claim 16 wherein each channel of the pair of channels is located on a side of the blade and has a substantially U-shaped cross section.

18. The intramedullary nail of claim 16 wherein each channel of the pair of channels has a substantially circular cross section with a diameter from about 0.8 to 3 mm.

19. An intramedullary nail for fixation of a fractured bone comprising:
   a helically twisted blade of predetermined thickness, length and width and having a distal end with a distal hole for receiving a first bone fixation element for securing the distal end to the bone and a proximal end with a proximal hole for receiving a second bone fixation element for securing the proximal end to the bone;
   a pair of channels in the blade for receiving a cable or wire for closing a fracture gap in the fractured bone; and
   a U-shaped cover at the distal end of the blade operatively associated with each channel of the pair of channels to allow the wire or cable to loop around from one of the channels to the other channel, wherein at least a portion of the blade has a flattened cross section.

20. An intramedullary nail for fixation of a fractured bone comprising:
   a helically twisted blade of predetermined thickness, length and width and having a distal end with a distal hole for receiving a first bone fixation element for securing the distal end to the bone and a proximal end with a proximal hole for receiving a second bone fixation element for securing the proximal end to the bone;
   a pair of channels in the blade for receiving a cable or wire for closing a fracture gap in the fractured bone; and
   a inner tube for receiving ends of the wire or cable and an outer tube for receiving the inner tube and having a threaded outer surface, wherein the proximal end of the blade includes a chamber having threaded walls for receiving the outer tube and rotation of the outer tube into the chamber tightens the wire or cable to close the fracture gap and wherein at least a portion of the blade has a flattened cross section.

* * * * *

UNITED STATES PATENT AND TRADEMARK OFFICE
CERTIFICATE OF CORRECTION

PATENT NO.   : 6,231,576 B1                                                Page 1 of 1
DATED        : May 15, 2001
INVENTOR(S)  : Robert Frigg; Silvana Filoso; Peter Däscher It is certified that error appears in the above-identified patent and that said Letters Patent is hereby corrected as shown below:

<u>Column 5,</u>
Line 43, replace "flatten" with -- flattened --.

Signed and Sealed this

Eighteenth Day of December, 2001

Attest:

Attesting Officer

JAMES E. ROGAN
*Director of the United States Patent and Trademark Office*